United States Patent [19]

Chague et al.

[11] Patent Number: 4,770,540

[45] Date of Patent: Sep. 13, 1988

[54] PROCESS AND APPLICATION FOR THE DETERMINATION OF TURBIDITY AND FLOW POINTS

[75] Inventors: Benoit Chague, St Genis Laval; Serge Esson, Vienne; Philippe Julliat, Taluyers, all of France

[73] Assignee: Societe Anonyme Elf France, France

[21] Appl. No.: 898,270

[22] Filed: Aug. 20, 1986

[30] Foreign Application Priority Data

Aug. 22, 1985 [FR] France ............... 85 12611

[51] Int. Cl.$^4$ ............... G01K 1/14; G01N 25/02
[52] U.S. Cl. ............... 374/17; 374/25; 374/186
[58] Field of Search ............... 374/16, 17, 19, 20, 374/25, 186, 12

[56] References Cited

U.S. PATENT DOCUMENTS

| | | | |
|---|---|---|---|
| 2,672,751 | 3/1954 | Luffer et al. | 374/25 |
| 3,479,859 | 11/1969 | Hager | 374/19 |
| 3,818,614 | 6/1974 | Meurer | 374/17 X |
| 4,368,991 | 1/1983 | Hentze et al. | 374/12 |
| 4,567,849 | 2/1986 | Wan | 374/12 X |
| 4,572,676 | 2/1986 | Biemans et al. | 374/17 |
| 4,603,979 | 8/1986 | Matilainen | 374/45 X |

OTHER PUBLICATIONS

French Standard, T 60–105, May 19, 1970.

Primary Examiner—Daniel M. Yasich
Attorney, Agent, or Firm—Ostrolenk, Faber, Gerb & Soffen

[57] ABSTRACT

Process for the determination of the turbidity point of a liquid, which consists in progressively cooling the liquid and noting the temperature at which turbidity appears; the temperatures at the center ($T_1$) and at the periphery ($T_2$) of the liquid are measured, their graphs as a function of time ($\theta$) are plotted and changes in the slope of these graphs are noted, the turbidity point being the temperature ($T_1$) at the center of the liquid which corresponds to the change in slope on the graph $T_2 - f'(\theta)$.

10 Claims, 4 Drawing Sheets

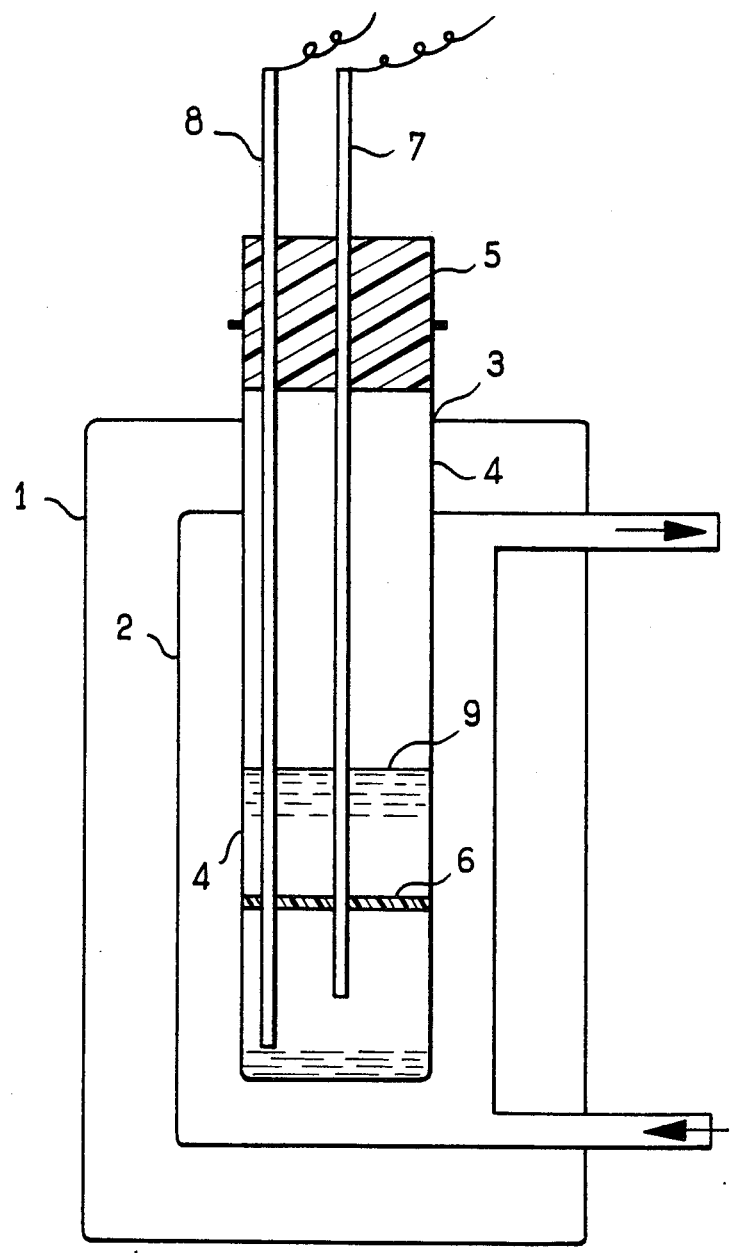
FIG_1

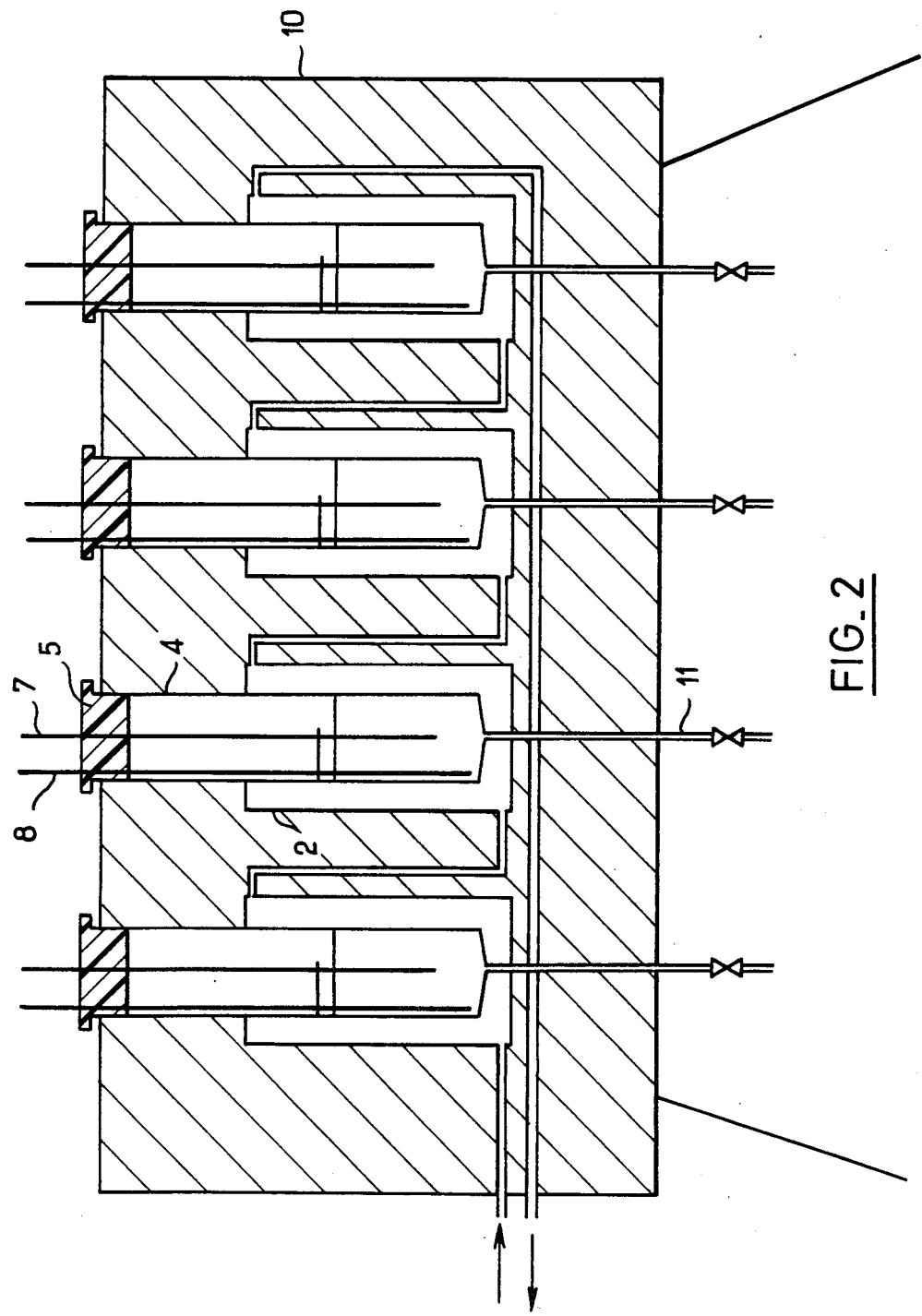

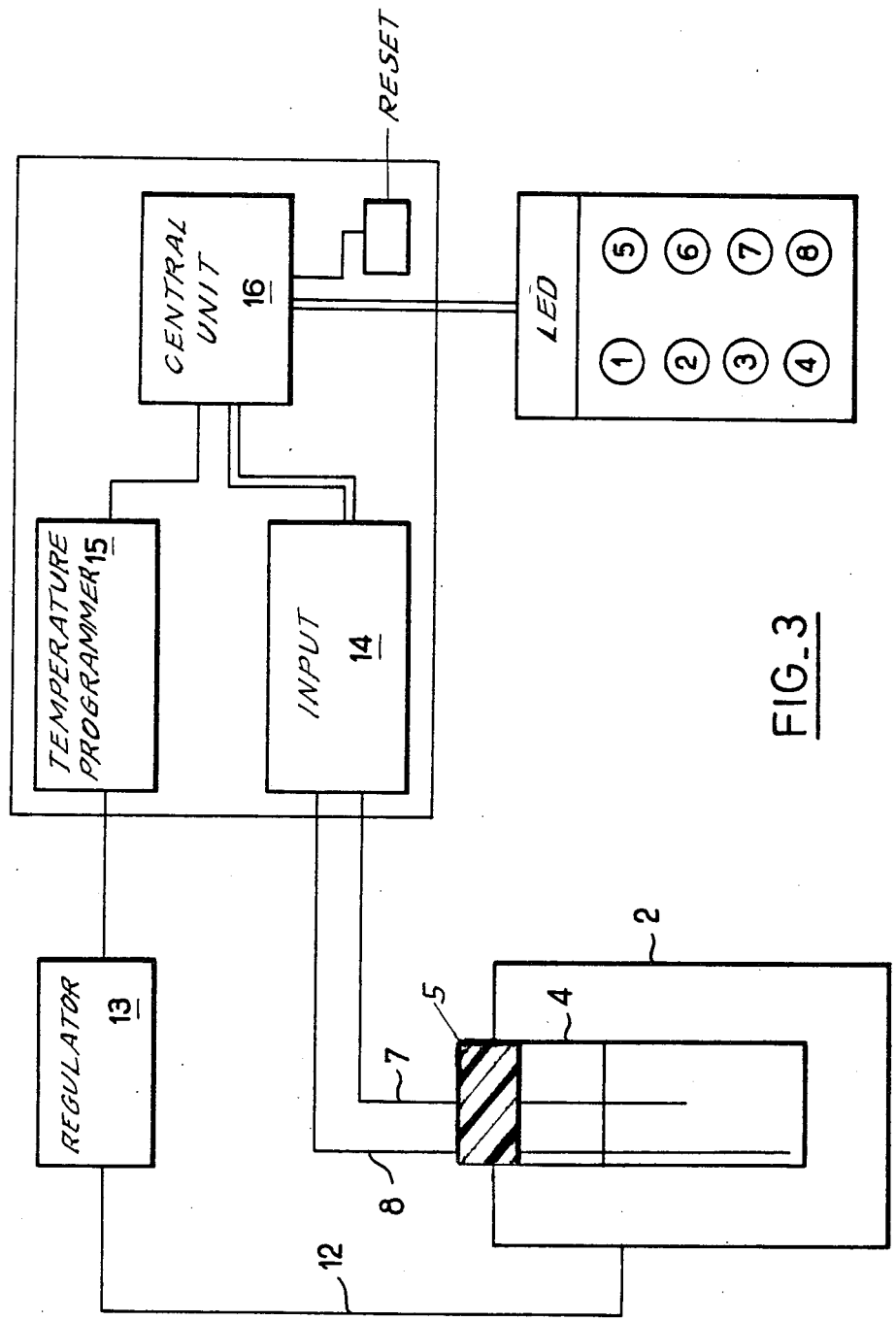
FIG_3

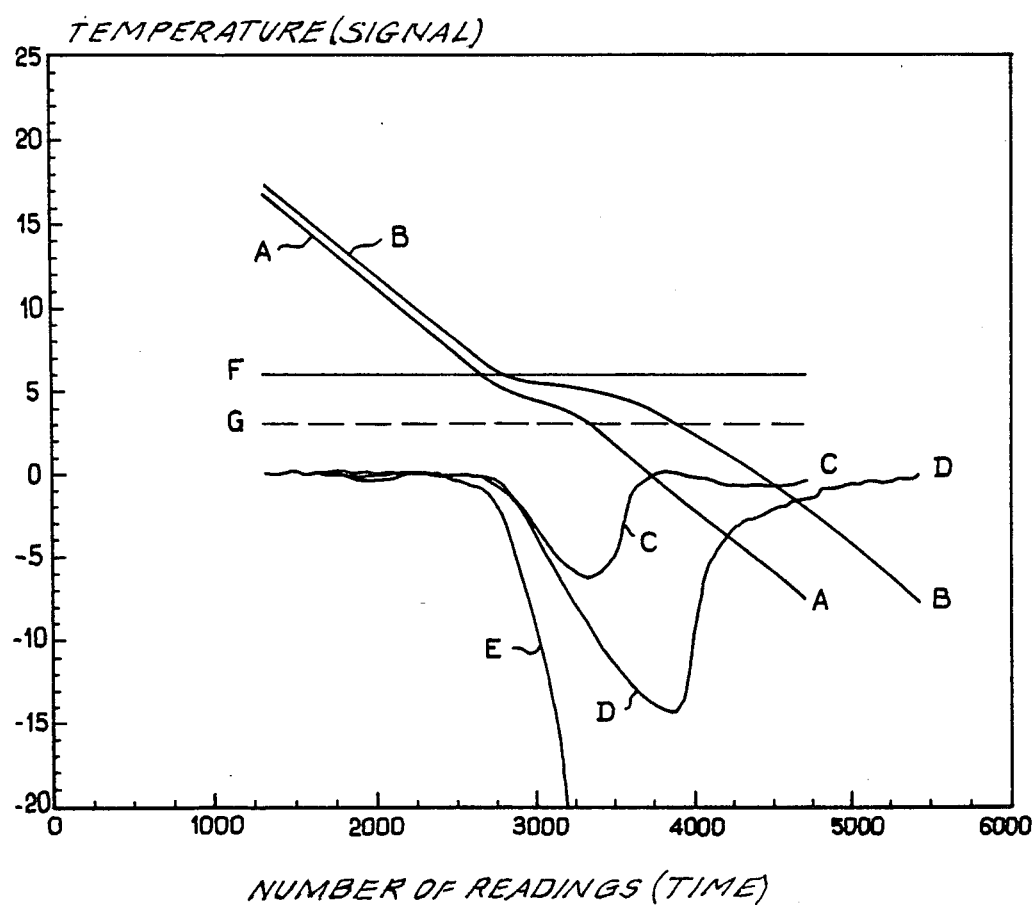
FIG_4

PROCESS AND APPLICATION FOR THE DETERMINATION OF TURBIDITY AND FLOW POINTS

The invention relates to an improved process and an apparatus for determination of the turbidity point and the flow point of various liquids, in particular those mixtures of hydrocarbons which comprise fuels, lubricating oils and crude petroleum. The invention can also be applied to determination of the temperature of the onset of crystallisation and to the freezing point of liquids.

Knowledge of the temperature at which a liquid begins to become turbid, because of the appearance within it of a solid phase, has importance in certain uses of the liquid. A typical case is that of fuels, the circulation of which can be obstructed below this temperature, because of the formation of solids. This also applies to a lubricating oil or a heat transmission liquid. Also, and for the same reason, it is important to know the flow temperature of a liquid, that is that at which normal movement of the liquid becomes possible. Also, there are official regulations and conditions which impose precise standards on the temperatures in question, particularly in relation to hydrocarbons, as regards various products utilized industrially.

Thus, determination of the turbidity point and the flow point of petroleum products is defined by French Standard T No. 60-105, published May 19, 1970, in particular for lubricating or fuel oils and gas oils. This standard also describes an apparatus of a particular shape and dimensions for operation of the standardized procedure. The apparatus comprises a cooling bath, in which a glass test tube is immersed vertically; the latter carries a stopper pierced in the centre to receive a thermometer which, thus centered in the tube, is located at its base. The tube, containing the liquid to be examined, is progressively cooled by the cooling bath. The standard requires the test-tube to be withdrawn rapidly, without disturbing its contents, each time the temperature reading has fallen by 1° C., in order to check the clarity of the liquid. The tube must then be replaced in the cooled jacket, the manual operations not lasting more than 3 seconds. The "turbidity point" is considered to be the temperature at which a distinct turbidity or cloudiness appears in the liquid at the base of the tube. With the same apparatus, the flow point of the liquid is determined according to Standard T 60-105; in this, observation of the tube, rapidly withdrawn from the bath, relates each time to the movement or immobility of the liquid in the tube when it is inclined. It is considered that the flow point is attained when the surface of the liquid does not deform for more than 5 seconds whilst the tube is held in a horizontal position. According to the standard, the flow point is the temperature reading plus 3° C. The beginning of the capillary part of the thermometer is 3 mm below the surface of the liquid.

As can be seen, the standard operations involve various operator factors which can affect unfavourably the accuracy and fidelity of the results. Visual appreciation of the turbidity gives rise to differences from one operator to another. The rapidity of the manipulations, their time being limited to 3 seconds etc, can also cause differences, depending upon the temperament of the persons carrying them out. This also applies to reading off the temperatures simultaneously with withdrawal of the tube. Thus, these manual/visual determinations take up time and, frequently in a control station, require the permanent presence of an operator.

The present invention has the object of improving the determinations described above in order to allow their rapid and precise realisation, with good repeatability, at less cost and freed from any operator factor. The invention in fact allows determination of the turbidity point and the flow point in total agreement with that given by operations effected according to Standard T-60 105, but with the advantages indicated below.

The process according to the invention for determining the turbidity point of a liquid, which consists in progressively cooling the liquid and noting the temperature at which turbidity appears, is characterised in that the temperatures at the centre ($T_1$) and at the periphery ($T_2$) of the liquid are measured, their graphs as a function of time ($\theta$) are plotted and changes in slope of these graphs are noted.

In accordance with the invention, the turbidity point is the temperature ($T_1$) at the centre of the liquid which corresponds to the change of slope of the graph $T_2 = f(\theta)$.

The flow point is defined by the value of the peripheral temperature ($T_2$) at the moment of an inflection in the curve $T_1 = f'(\theta)$.

Changes in slope of the temperature graphs are due to thermal effects caused during the formation of turbidity, particularly because of crystallisation of the heavier paraffins in an oil or gas oil.

The flow point of gas oils corresponds as a maximum to this exothermic effect. As electronic means nowadays allow the recordal and easy processing of such information, the present invention can be carried out in a simple and continuous fashion, without the tedious manipulations of standardised methods, by the use of a micro-processor.

Moreover, due to the double measurement of temperature at the centre of the liquid and at its periphery, the invention makes possible the simultaneous determination of the turbidity and flow points.

The invention is illustrated non-limitatively by the following description of an apparatus allowing the process described to be readily carried out.

FIG. 1 shows diagrammatically in axial section a cooled test-tube and its accessories, where the temperature measurements are carried out.

FIG. 2, also a diagrammatic axial section, shows an assembly of four stations for determining the turbidity and flow points.

FIG. 3 is a diagram of an electronic system serving the test device of FIG. 1.

FIG. 4 shows by way of example the graphs of temperature $= f$(time) in a particular case of determination of the turbidity and flow points by the process of the invention.

FIG. 1 shows an evacuated container 1 surrounding a reservoir 2, in which a cooling fluid continuously circulates, as indicated by the arrows. Through an opening 3 at the top of the container 1, a thermostatic, or regulated, controllable test-tube 4 dips into the cooling fluid.

The thermally conductive test-tube 4 is closed by a stopper 5 of polytetrafluoroethylene, through which pass the rods of two thermoelectric couples or Pt 100 temperature probes 78. These probes pass through a support 6 of plastics material, particularly of polytetrafluoroethylene. The active part of the probe 7 dips into the lower central region of the liquid 9 in the test-tube 4, while that of the probe 8 is located near the base and the exterior wall of the test-tube.

In a particular embodiment, the container 1 has a diameter of 80 mm and a height of 130 mm; the diameter of the reservoir 2 is 50 mm and its height is 100 mm; the test-tube 4 has a diameter of 30 mm and a height of 120 mm, a line 9 indicating the level of the liquid being located 50 mm above the base.

FIG. 2 shows a body 10 filled with thermal insulation, in which four cooling fluid reservoirs 2 are located, connected in series. A test-tube 4' similar to that of FIG. 1, except that it is provided with a purge 11, allowing the tube to be emptied of its liquid without withdrawing it, dips into each of the reservoirs. Thus, an assembly of four test stations is provided, allowing a series of four determinations of the turbidity and flow points to be carried out simultaneously.

In FIG. 3, the principal parts of a microprocessor connected to the apparatus of FIG. 1 are indicated diagrammatically. As micro-processors are well known, there is no need for a detailed description. It will merely be noted that the programmer 15 directs the commands of the regulator 13 to the bath. The electrical signals from the temperature probes 7 and 8 are received in an input circuit 14 in order to be processed in a central unit 16, to which the temperature programmer 15 is also connected.

Operation of the apparatus according to the invention, in the case where the four stations of FIG. 2 are employed, comprises the following steps. The liquid to be studied is preheated to a temperature 20° to 25° C. above the presumed turbidity point and it is then poured into the test-tube up to the gauge level provided. The test-tube 4 is then put into the cryogenic bath 2 and the probes 7 and 8 are located as indicated in FIGS. 1 and 2.

The micro-processor system is switched on by pressing an appropriate key, which causes the apparatus to carry out the following: Control of the cooling bath temperature, test of the probe 7 at the first station, receipt of the temperatures of the four stations, processing to detect the turbidity and flow points.

The micro-processor keys (1 to 4 in FIG. 3) allow selection of the probe 7, the probe 8, the turbidity and flow points and the point of the onset of crystallisation, as well as the start of the analysis.

Other keys (5 to 8, FIG. 3) allow the respective selection of each of the four stations of the apparatus. When a flow point is detected, it is indicated. When all the turbidity and flow points are detected, they can be read off from the keys 2, 5, 6, 7 and 8 of FIG. 3.

A reset key allows repetition of an operation.

The diagram of FIG. 4 comprises a series of graphs relating to the simultaneous determination of the turbidity point and the flow point of a gas oil, taken by way of example, with the aid of the automatic apparatus described above.

The abscissae are the numbers of readings made with the liquid in the test-tube 4 during constant cooling at 1° per minute. The readings are made at equal time intervals, their number being equivalent to the predetermined time periods. As the ordinates, the temperatures measured by the thermometric probes 7 and 8 are indicated.

The line A represents variations in the temperature $T_2$ indicated by the probe 8 adjacent the wall of the test-tube 4, as a function of time, or $T_2 = f(\theta)$.

The very clear change in slope of the line A at 2850 readings detects the crystallisation of a component of the medium. The corresponding temperature, that is the turbidity point, is read off on the line B for the same abscissa. This indication tallies with the horizontal line F, which corresponds to the turbidity point for the same gas oil, determined in accordance with the standards.

The line B shows variations in the temperature $T_1$ received from the central probe 7, as a function of time, or $T_1 = f'(\theta)$. Its marked change of slope around 3200 readings corresponds to the flow point $T_2$, which is given by the probe 8 at the same time (same number of readings) that is, for the same abscissa. Compared with the ordinate of the line G, this temperature $T_2$ is in agreement with the value of the flow point found according to the standards (G).

According to a preferred feature of the invention, in order to note more accurately inflections in the graphs of types A and B, their derivatives are also plotted, namely the lines such as C and D. The first curve on each of these derived lines C and D indicates the appearance of a solid phase. Thus the first curve (to the left), which is clearer than on the graphs A and B, that is the first change of slope on C, indicates the turbidity point, the value of which is given by a corresponding graph of the type B at the same abscissa. In an analogous fashion, the flow point is given with greater clarity by the derived curve D and evaluated on A. It is to be noted, in the Example illustrated that the lines C and D represent derivatives of the graphs A and B filtered and set out with a displacement of the abscissae.

The invention preferably also comprises the trace of a cumulative line E, in order to avoid the detection of parasite changes and phenomena, which are not really due to solidifications taking place within the liquid studied. This line E constitutes the sum of the graph C reset to zero each time the latter undergoes deviations between certain predetermined limits. Thus, detection of the turbidity point is only valid if the ordinate of the line E exceeds a certain pre-established threshold. Detection of the flow point is made after determination of the turbidity point.

We claim:

1. A method of determining the turbidity point of a liquid comprising the steps of:
   (a) placing the liquid in a thermostatically controllable measuring device at a temperature above that of the expected turbidity point;
   (b) uniformly cooling the liquid;
   (c) periodically measuring the temperature at about the center of the liquid and plotting a graph of the measured temperature as a function of time;
   (d) periodically measuring the temperature in the liquid near an inner wall of the device and plotting the measured temperature as a function of time;
   (e) determining the abcsissa of the first change in slope of the inner wall plot and
   (f) determining the temperature corresponding to the point of the center plot having the same abscissa as determined in step (e), said temperature being turbidity point of the liquid.

2. The method according to claim 1 in which the frequency of measuring the temperature at the center and near the inner wall are the same.

3. A method according to claim 2 wherein the liquid is cooled at a rate of 1° per minute.

4. A method according to claim 3 in which both of such temperature measurements are carried out continuously.

5. A method according to claim 1 in which the flow point of the liquid is additionally determined by determining the abscissa of the first change in slope of the liquid center plot and determining the temperature corresponding to the point in the inner wall liquid plot having the same abscissa, said temperature being the flow point of the liquid.

6. A method according to claim 1 in which at least one of the plottings of the temperature as a function of time includes plotting of the rate of change in temperature as a function of time.

7. An apparatus for the determination of the turbidity point of a liquid which comprises, in combination, a thermally conducting first container for the liquid to be measured, means supporting said first container in a fluid cooling second container to uniformly change the temperature of liquid in the container, first temperature measuring means disposed through a stopper of said first container at about the geometric middle of the liquid when in the container, second temperature measuring means disposed near the bottom and an inner wall of the first container, means for recording the temperature measured by the first temperature measuring means as a function of time and means for recording the temperature measured by the second temperature measuring means as a function of time for determining the turbidity point of the liquid.

8. Apparatus according to claim 7 wherein said container has a test tube shape and is disposed within a thermally insulating container and said apparatus includes means for circulating a heat exchange fluid in the space between said container and said thermally insulating container.

9. Apparatus according to claim 8 containing a plurality of said thermally conducting containers within said thermally insulating container.

10. Apparatus according to claim 9 in which each of said means for recording the temperature are connected to a microprocessor adapted to record data and plot the data recorded on graphs having the same abscissa.

* * * * *